(12) United States Patent
Sugimura et al.

(10) Patent No.: US 9,372,189 B2
(45) Date of Patent: Jun. 21, 2016

(54) BIOMARKER FOR LYMPHOCYTIC INFUNDIBULONEUROHYPOPHYSITIS, AND USE APPLICATIONS THEREOF

(71) Applicant: National University Corporation Nagoya University, Nagoya-shi (JP)

(72) Inventors: Yoshihisa Sugimura, Nagoya (JP); Yutaka Oiso, Nagoya (JP); Shintaro Iwama, Nagoya (JP); Atsushi Enomoto, Nagoya (JP); Takuya Kato, Nagoya (JP)

(73) Assignee: NATIONAL UNIVERSITY CORPORATION NAGOYA UNIVERSITY, Nagoya-Shi (JP)

( * ) Notice: Subject to any disclaimer, the term of this patent is extended or adjusted under 35 U.S.C. 154(b) by 58 days.

(21) Appl. No.: 14/360,701

(22) PCT Filed: Nov. 16, 2012

(86) PCT No.: PCT/JP2012/079776
§ 371 (c)(1),
(2) Date: Oct. 31, 2014

(87) PCT Pub. No.: WO2013/080811
PCT Pub. Date: Jun. 6, 2013

(65) Prior Publication Data
US 2015/0160209 A1    Jun. 11, 2015

(30) Foreign Application Priority Data
Nov. 28, 2011   (JP) ................. 2011-258387

(51) Int. Cl.
G01N 33/53    (2006.01)
G01N 33/564   (2006.01)
C07K 16/18    (2006.01)

(52) U.S. Cl.
CPC .............. *G01N 33/564* (2013.01); *C07K 16/18* (2013.01); *G01N 2333/4703* (2013.01); *G01N 2800/28* (2013.01)

(58) Field of Classification Search
None
See application file for complete search history.

(56) References Cited

PUBLICATIONS

Kato et al., Physical and Functional Interaction of Rabphilin-3A with a-Actinin, The Journal of Biological Chemistry, Vo.. 271, No. 50, 1996, pp. 31775-31778.*
Strongin, Laboratory Diagnosis of Viral Infections, Sensitivity, Specificity, and Predictive Value of Diagnostic Tests: Definitions and Clinical applications, Lennette, ed. Marcel Dekker, Inc. New York, pp. 211-219, 1992.*
Damien T. O'Dwyer et al., "Identification of the 49-kDa Autoantigen Associated with Lymphocytic Hypophysitis as α-Enolase," J Clin Endocrinol Metab. 87(2): 2002, pp. 752-257.
Toshihiro Takao et al., "Antipituitary Antibodies in Patients with Lymphocytic Hypophysitis," Horm Res. 55(6): 2001, pp. 288-292.
Susumu Tanaka et al., "Detection of autoantibodies against the pituitary-specific proteins in patients with lymphocytic hypophysitis," Eur J Endocrinol. 147(6):2002, pp. 767-775.
S. Bensing et al., "Lymphocytic hypophysitis: Report of two biopsy-proven cases and one suspected case with pituitary autoantibodies," J Endocrinol Invest, 30(2): 2007, pp. 153-162.
Isabella Lupi et al., "Novel autoantigens in autoimmune hypophysitis," Clin Endocrinol. 69(2): 2008, pp. 269-278.
International Search Report mailed Dec. 18, 2012, issued for PCT/JP2012/079776.
Jinn-Shiun Chen et al., "Detection of autoantibodies against Rabphilin-3A-like protein as a potential biomarker in patient's sera of colorectal cancer", Clinica Chimica Acta, Elsevier BV, vol. 412, No. 15, Apr. 12, 2011, pp. 1417-1422.
Hiroki Hirai et al., "Selective screening of secretory vesicle-associated proteins for autoantigens in type 1 diabetes: VAMP2 and NPY are new minor autoantigens", Clinical Immunology, vol. 127, No. 3, Jun. 1, 2008, pp. 366-374.
Akira Shimazu et al., "Clinical features and diagnosis of 'lymphocytic' infundibulo-hypophysitis", Folia Endocrinologica Japonica, vol. 88, No. Supplement-2, Aug. 1, 2012, pp. 68-78.
Supplementary European Search Report dated Jun. 23, 2015, issued for the European patent application No. 12853028.4.

* cited by examiner

*Primary Examiner* — Gary W Counts
(74) *Attorney, Agent, or Firm* — Locke Lord LLP; James E. Armstrong, IV; Nicholas R. Herrel

(57) ABSTRACT

The purpose of the present invention is to provide: a biomarker specific to lymphocytic infundibuloneurohypophysitis; and use applications of the biomarker. Provided are: a biomarker comprising an anti-rabphilin 3a antibody; and a test method using the biomarker.

11 Claims, 6 Drawing Sheets

Fig. 2

LINH ····· 9 cases   8/9

LAH ····· 3 cases   0/3

IgG4-related hypophysitis ····· 3 cases   1/3

Disease control ····· 10 cases   1/10
    Germ cell tumor + DI   3 cases   1/3
    After surgery of suprasellar of pineal tumor + DI   1 case   0/1
    After surgery of hypothalamus tumor + DI   1 case   0/1
    Rathke's cleft cyst + DI   1 case   0/1
    Craniopharyngioma + DI   2 cases   0/2
    After surgery of Glioma + DI   1 case   0/1
    Sarcoidosis + DI   1 case   0/1

Healthy control ··· 10 cases   1/10

All Cases
Sensitivity 88.9% (8/9)
Specificity 87.0% (20/23)
88.5% (23/26)

↑ Value including IgG4

Discrimination from tumor lesion + DI
  Specificity 90% (9/10)

Fig. 4
Posterior pituitary
AVP          Rabphilin 3a         merge
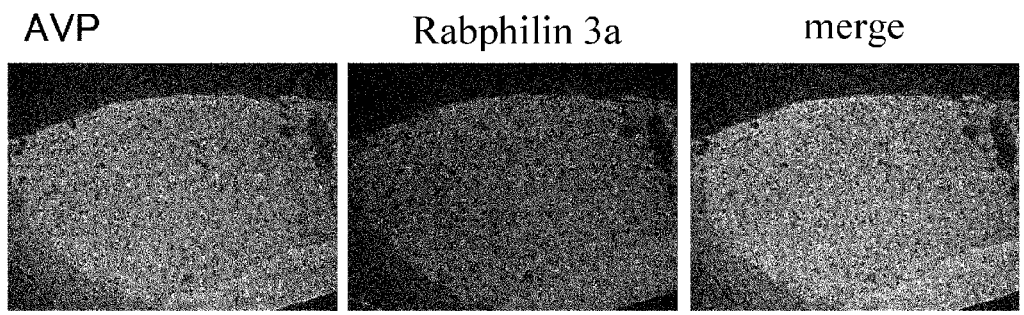
SON
AVP          Rabphilin 3a         merge
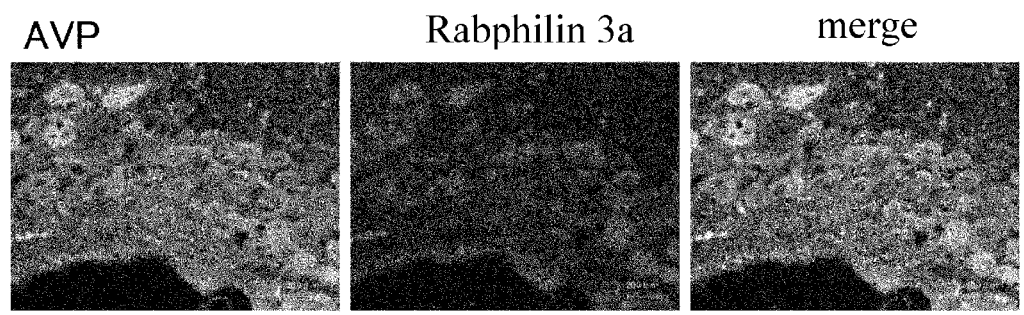

Fig. 5

| | | | |
|---|---|---|---|
| Lymphocytic infundibuloneurohypophysitis | 11/12 | Healthy subject | 3/12 |
| Lymphocytic adenohypophysitis | 0/5 | | |
| Lymphocytic hypophysitis | 2/6 | | |
| IgG4-related hypophysitis | 2/5 | | |
| Idiopathic central diabetes insipidus | 0/6 | Autoimmune disease | 7/69 |
| | | Mixed connective-tissue disease | 0/2 |
| | | Multiple myositis/dermatomyositis | 0/8 |
| After surgery of cerebral tumor DI | 1/14 | Chorionitis | 1/14 |
| Germ cell tumor | 1/4 | Chronic Arthritis rheumatoid | 4/20 |
| After surgery of suprasellar of pineal tumor | 0/1 | Sjogren syndrome | 1/10 |
| | | SLE | 1/15 |
| After surgery of hypothalamus tumor | 0/1 | Healthy subject (foreigner) | 5/30 |
| Rathke's cleft cyst | 0/2 | | |
| Craniopharyngioma | 0/2 | | |
| After surgery of Glioma | 0/1 | | |
| After surgery of teratoma | 0/2 | | |
| Sarcoidosis | 0/1 | | |
| Empty sella DI | 0/1 | | |
| Isolated ACTH deficiency | 2/5 | | |

FIG. 6

All cases

Sensitivity 91.7% (11/12)
Specificity 85.6% (131/153)

Discrimination from tumor lesion + DI

Specificity 92.8% (13/14)

Discrimination between other autoimmune disease and LINH

Specificity 95.2% (20/21)

Discrimination between other autoimmune disease and LINH

Specificity 89.9% (62/69)

Discrimination between healthy subject and LINH

Specificity 80.9% (34/42)

BIOMARKER FOR LYMPHOCYTIC INFUNDIBULONEUROHYPOPHYSITIS, AND USE APPLICATIONS THEREOF

TECHNICAL FIELD

The present invention relates to a biomarker for lymphocytic infundibuloneurohypophysitis, and more specifically to a biomarker for lymphocytic infundibuloneurohypophysitis and an assay using the biomarker. This application is based upon and claims the benefit of priority from prior Japanese Patent Application No. 2011-258387, filed Nov. 28, 2011, the entire contents of which are incorporated herein by reference.

BACKGROUND ART

Lymphocytic hypophysitis is an autoimmune chronic inflammatory disease caused by infiltration of lymphocytes and plasmacytes into the hypothalamic infundibulum and pituitary. Lymphocytic infundibuloneurohypophysitis (hereinafter abbreviated as "LINH") is a disease accompanied by inflammation limited to infundibulum and posterior lobe, and shows central diabetes insipidus. The diagnosis of LINH is sometimes difficult, and its definite diagnosis requires biopsy of the pituitary. However, such diagnosis is invasive and thus is scarcely carried out, and not a few subjects are erroneously diagnosed and subjected to needless surgery. The etiology of the disease is unknown, and there is no established therapy.

Some diagnostic markers (biomarkers) for lymphocytic hypophysitis are reported (for example, see Non-Patent Literatures 1 to 5), but none of them is clinically applied because none of them combines high sensitivity and high specificity. In addition, there is no report on the diagnosis marker specific to LINH.

PRIOR ART DOCUMENT

Non-Patent Document

Non-patent Literature 1: J Clin Endocrinol Metab. 87 (2): 752-7, 2002
Non-patent Literature 2: Horm Res. 55 (6): 288-92, 2001
Non-patent Literature 3: Eur J Endocrinol. 147 (6): 767-75, 2002
Non-patent Literature 4: J Endocrinol Invest, 30 (2): 153-62, 2007
Non-patent Literature 5: Clin Endocrinol. 69 (2): 269-78, 2008

SUMMARY OF THE INVENTION

Problem to be Solved by the Invention

In consideration of the above-described background, the present invention is intended to provide an LINH-specific biomarker and applications thereof, more specifically the technique useful for the examination of LINH, thereby allowing the discrimination of LINH and highly confident diagnosis. Specifically, the purpose of the present invention is to provide a biomarker useful for the examination of LINH, an assay using the biomarker, and a test reagent used in the assay.

Means for Solving Problem

The inventors made investigations for finding an LINH-specific biomarker. Specifically, firstly, serums were collected from LINH patients, disease control subjects showing central diabetes insipidus because of, for example, cerebral tumor, and healthy subjects, and IgG was purified. On the other hand, an extract of posterior pituitary protein was prepared from rat pituitary. The IgG purified from the serum and the extract of posterior pituitary protein was mixed, and subjected to immunoprecipitation using protein G beads, and then the antigen was eluted from the immune precipitate. The eluted antigen was subjected to analysis (shotgun proteomics) using an LC-MS/MS system, Pradigm MS4-PAL-LTQ Orbitrap XL (Thermo Fisher Scientific Inc.). The MS data was analyzed using a public database and an analysis software, and the potential autoantigen protein was identified. Secondly, recombinant proteins were synthesized for six proteins as autoantigen protein candidates, and then the reactivity between these recombinant proteins and the serums of the patients was studied by the Western blot method. As a result of this, an autoantibody against rabphilin 3a was found in eight subjects of the nine LINH patients (8/9). On the other hand, the cases wherein the autoantibody was found in the control were 1/10 for the healthy subjects, 0/3 for the subjects with lymphocytic adenohypophysitis, 1/3 for the subjects with IgG4-related hypophysitis accompanied by diabetes insipidus, and 1/10 for the subjects with diabetes insipidus accompanying tumor and others. Accordingly, rabphilin 3a was proved to be an autoantigen having high specificity to LINH. In other words, it has been proved that the autoantibody (anti-rabphilin 3a antibody) against rabphilin 3a is markedly useful as a biomarker for LINH, and that the use of the antibody as the indicator allows the examination of LINH (for example, examination for discrimination) with markedly high sensitivity and high specificity.

As a result of further study, it was found that rabphilin 3a is expressed also in the rat hypothalamic paraventricular nuclei, supraoptic nuclei, and posterior pituitary. This finding suggests that rabphilin 3a is directly involved in the pathogenesis of LINH, and proved that the autoantibody against the molecule, more specifically the anti-rabphilin 3a antibody is useful for grasping the disease state of LINH.

As a result of study using more specimens, markedly high specificity was found in the discrimination between diabetes insipidus (DI) accompanying to tumor lesion and LINH, and the discrimination between idiopathic or secondary central diabetes insipidus and LINH, in addition, high specificity was found also in the discrimination of other autoimmune disease and LINH. Therefore, it was further corroborated that the anti-rabphilin 3a antibody is useful as a biomarker for LINH. The following aspects of the present invention are mainly based on the above-described facts.

[1] A lymphocytic infundibuloneurohypophysitis marker including an anti-rabphilin 3a antibody.

[2] An assay for lymphocytic infundibuloneurohypophysitis, using the level of an anti-rabphilin 3a antibody in a specimen as an indicator.

[3] The assay according to [2], which includes the following steps (1) to (3):

(1) a step of providing a specimen derived from a subject;
(2) a step of detecting an anti-rabphilin 3a antibody in the specimen; and
(3) a step of determining whether the developed disease is lymphocytic infundibuloneurohypophysitis or not, or the possibility of developing lymphocytic infundibuloneurohypophysitis, based on the detection result.

[4] The assay according to [3], wherein the high level of the anti-rabphilin 3a antibody is used as the indicator showing that the developed disease is lymphocytic infundibuloneurohypophysitis, and as the indicator showing that the possibility of developing lymphocytic infundibuloneurohypophysitis is high.

[5] The assay according to [3] or [4], wherein the determination in the step (3) is carried out based on the comparison between the detected value obtained in the step (2) and the detected value obtained in the control specimen.

[6] The assay according to [3] or [4], wherein the determination in the step (3) is carried out based on the comparison between the detected value obtained in the step (2) and the detected value in the specimen taken from the same subject in the past.

[7] The assay of according to any of [2] to [6], wherein the specimen is blood, plasma, serum, cerebrospinal fluid, or urine.

[8] A test reagent for lymphocytic infundibuloneurohypophysitis, including rabphilin 3a or its antibody-binding fragment.

[9] A kit for testing lymphocytic infundibuloneurohypophysitis, including the lymphocytic infundibuloneurohypophysitis test reagent according to [8].

BRIEF DESCRIPTION OF DRAWING

FIG. 2 shows the summary of the autoantibody positive rate for rabphilin 3a. The proportion of the positive subjects was shown for each disease. For example, 8/9 indicates that eight of nine subjects were autoantibody-positive.

FIG. 4 shows the expression of an LINH-specific antigen. The immunohistochemistry of rat posterior pituitary (upper row), and hypothalamic supraoptic nucleus (SON) (lower row). The localization of AVP (left) and rabphilin 3a (center) was studied. The right is the merge of two images.

FIG. 5 shows the summary of the autoantibody positive rate for rabphilin 3a. Using more specimens, the usefulness of rabphilin 3a was studied. The autoantibody positive rate was studied also for the specimens of autoimmune disease patients.

FIG. 6 shows the summary of the sensitivity and specificity of discrimination.

Figure 1:
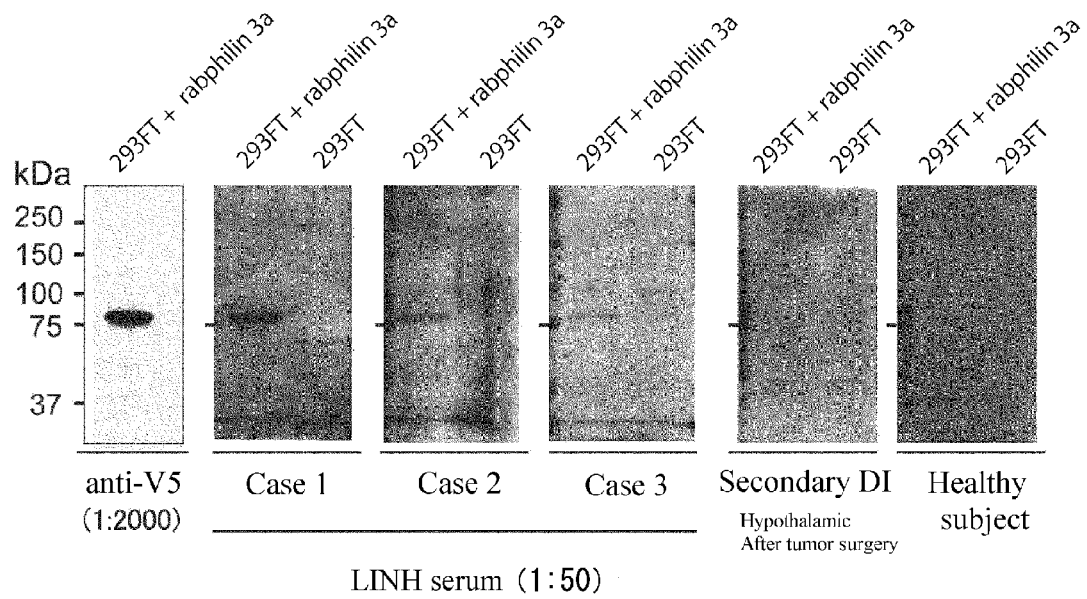
FIG. 1 shows the result of a Western blot test using the blood serums of the patients and rabphilin 3a. Reaction to rabphilin 3a was found in the LINH patients (subjects 1 to 3). On the other hand, similar reaction was not found in secondary diabetes insipidus (DI) or healthy subjects.

DESCRIPTION OF EMBODIMENT (First Aspect of the Present Invention: Biomarker for Lymphocytic Infundibuloneurohypophysitis (LINH))

A first aspect of the present invention relates to a biomarker for LINH (hereinafter may be referred to as "the biomarker of the present invention"). The biomarker of the present invention is a useful indicator for the discrimination of LINH, or for evaluating the possibility of developing LINH. The term "discrimination" herein means the determination whether the disease developed in the subject is LINH or other disease. Especially, the biomarker of the present invention is useful for ascertaining whether the patient with diabetes insipidus has LINH or not. In particular, the biomarker of the present invention is important as an indicator for discriminating central diabetes insipidus accompanying LINH and diabetes insipidus accompanying tumor lesion.

"Possibility of developing LINH" includes current and future possibilities of developing LINH. The "current possibility of developing LINH" represents whether LINH is developed or not, or the probability of developing LINH at the time of assay. On the other hand, "future possibility of developing LINH" represents the future possibility (risk) of developing LINH.

The biomarker of the present invention is composed of an antibody (autoantibody) against an LINH-specific antigen molecule rabphilin 3a, more specifically an anti-rabphilin 3a antibody. Rabphilin 3a is a protein coded by an RPH3A gene. Rabphilin 3a is an effector of RAB3A, and known to participate in the exocytosis of neurotransmitters and hormones. The amino acid sequence of rabphilin 3a (DEFINITION: *Homo sapiens* rabphilin 3A homolog (mouse), mRNA (cDNA clone MGC: 29559 IMAGE: 3510158), complete cds. ACCESSION: BC017259) and the nucleotide sequence coding the amino acid sequence are set forth in SEQ ID NO. 1 and SEQ ID NO. 2 in the sequence list, respectively. As a general rule, the biomarker of the present invention is not the anti-rabphilin 3a antibody existing in a living body, but the anti-rabphilin 3a antibody in a specimen taken from (or separated from) a living body.

(Second Aspect of the Present Invention: LINH Assay)

A second aspect of the present invention relates to a use of the biomarker of the present invention, and provides a method for testing whether the developed disease is LINH or not, or the possibility of developing LINH (hereinafter may be referred to as "the assay of the present invention"). The assay of the present invention allows the discrimination of LINH (when determining whether the developed disease is LINH or not). The assay of the present invention is useful as a means for determining whether LINH is developed not at present, or a means for evaluating the possibility of developing LINH in future (when the possibility of developing LINH is determined). Thus, the assay of the present invention provides useful information for the diagnosis of LINH. The assay of the present invention is, for example, useful for simple and objective definite diagnosis of LINH.

In the assay of the present invention, the level of the biomarker of the present invention in the specimen derived from the subject is used as the indicator. The "level" herein typically means "amount" or "concentration". However, according to convention and technical common knowledge, the term "level" is used also when showing whether the biomarker of the present invention can be detected or not (more specifically the presence or absence of apparent presence).

The assay of the present invention includes the following steps:

(1) a step of providing a specimen derived from a subject;
(2) a step of detecting an anti-rabphilin 3a antibody in the specimen;
(3) a step of determining whether the developed disease is lymphocytic infundibuloneurohypophysitis or not, or the possibility of developing lymphocytic infundibuloneurohypophysitis, based on the detection result.

In the step (1), a specimen derived from the subject is provided. The specimen may be, for example, blood, plasma, serum, cerebrospinal fluid, or urine of the subject. The subject is not particularly limited. More specifically, the present invention is widely applicable to the subject requiring the discrimination of LINH, and the subject requiring the determination of the possibility of developing LINH at present or in future (more specifically, whether LINH is developed or not, the degree of possibility of having LINH, and the degree of possibility of developing LINH in future). For example, the subjects having the symptom of central diabetes insipidus correspond to "the subject requiring the discrimination of LINH". In addition, when the present invention is applied to the patient who has been diagnosed to have LINH based on health questionnaire or other test by physician, the propriety of the diagnosis can be determined based on an objective indicator, or the level of the biomarker. More specifically, according to the assay of the present invention, information aiding or supporting the prior art diagnosis can be obtained. This information is useful for the determination of more appropriate course of treatment, and promotes the improvement of therapeutic effect and the patient's QOL (quality of life). On the other hand, the present invention may be used for monitoring the disease state, thereby preventing the increase of the difficulty of treatment, seriousness, and recurrence.

The subjects in whom hyperplasia of the pituitary stalk or pituitary enlargement is found by image examination such as MRI examination are presumed to have high risk of developing LINH (high risk subjects), and are suitable subjects. The application of the present invention to these subjects before the development of the symptom of LINH allows prevention or delay of the development, or therapeutic intervention in the early stage. The present invention is useful for specifying the subjects having high risk of developing LINH. Such specification is allows the decrease of possibility of developing LINH (the possibility of having LINH) by, for example, precautions or improvement of lifestyle habits. Those having no subjective symptom, who can't be or is hard to be determined whether having LINH or not by prior art diagnosis, are also preferred subjects of the present invention. The present invention may be carried out as an item of health examination.

In the step (2), the biomarker in the specimen is detected. It is not essential to strictly determine the biomarker level. More specifically, the biomarker level is detected so as to allow the determination in the subsequent step (3). For example, the detection may be carried out so as to allow the determination whether the biomarker level in the specimen exceeds the specified value.

The method for detecting the biomarker is not particularly limited, but is preferably an immunological method. Immunological methods allow prompt and highly sensitive detection. In addition, the operation is simple. The measurement by an immunological method uses a substance which specifically binds to the biomarker. As the substance, in typical cases, rabphilin 3a or its antibody-binding fragment is used. The "antibody-binding fragment" is a fragment of rabphilin 3a containing the epitope binding to the anti-rabphilin 3a antibody, and binds to the anti-rabphilin 3a antibody in the same manner as full length rabphilin 3a.

Examples of the measurement method include latex agglutination assay, fluoroimmunoassay (FIA method), enzyme immunoassay (EIA method), radioimmunoassay method (RIA method), and Western blot method. Examples of preferred measurement methods include the FIA method and EIA method (including ELISA method). These methods allow highly sensitive, prompt, and simple detection. The FIA method uses a fluorescent-labeled antibody, and detects an antigen-antibody complex (immune complex) using fluorescence as the signal. On the other hand, the EIA method uses an enzyme-labeled antibody, and detects an immune complex using the color development or luminescence based on enzyme reaction as the signal.

The ELISA method has many advantages such as high detection sensitivity, high specificity, marked quantitative performance, simple operation, and suitability for simultaneous treatment of many specimens. An example of the specific operation method for using the ELISA method is shown below. Firstly, the anti-rabphilin 3a antibody prepared by immunizing a rabbit or goat is immobilized on an insoluble support. Specifically, for example, the surface of a microplate is immunized (coated) by an anti-rabphilin 3a antibody. The antibody thus solid-phased is brought into contact with the specimen and enzyme-labeled rabphilin 3a. As a result of this operation, the solid-phased antibody binds to the rabphilin 3a to form an immune complex. However, if the anti-rabphilin 3a antibody (autoantibody) is present in the specimen, it competes with the solid-phased antibody, whereby the bonding amount between the solid-phased antibody and rabphilin 3a decreases. After removing the non-specific binding component by washing operation, color is developed by the reaction with a substrate of the enzyme. Subsequently, the immune complex is detected using the amount of color development as the indicator. Details about the ELISA method are described in many publications and literatures, and they may be referred when the experimental method and experimental condition are established. The method may be competitive or non-competitive. Alternatively, a method including contacting the specimen with the solid-phased rabphilin 3a (or its antibody-binding fragment) to form an immune complex, and then detecting the immune complex using a secondary antibody or the like, or a sandwich method may be used.

Alternatively, a means such as a protein array or protein chip which can detect many specimens simultaneously may be used.

In the step (3), whether the developed disease is LINH or not is determined based on the detection result. In other embodiment, the possibility of developing LINH is determined based on the detection result. In order to allow highly accurate determination, it is preferred that the determination be carried out after comparing the detected value obtained in the step (2) with the detected value of the control specimen (control). The control specimen may be, for example, a specimen from a healthy subject, a specimen from a patient with diabetes insipidus accompanying tumor lesion, a specimen from a patient with idiopathic or secondary central diabetes insipidus, or a specimen from a patient with other autoimmune disease. The determination may be qualitative or quantitative. As is apparent from the criteria, the determination herein may be carried out automatically/mechanically without depending on the judgment by a specialist such as a physician or laboratory technician.

(Example of Qualitative Determination 1: Discrimination)

The determination that "the developed disease is LINH" is made when the detected value (for example, labeled amount or fluorescence amount) is higher than the standard value, and the determination that "the developed disease is not LINH" is made when the detected value is lower than the standard value. When discrimination from a specific disease is made, in typical cases, the determination that "the developed disease is LINH" is made when the detected value is higher than the standard value, and the determination that "the developed disease is the specific disease" is made when the detected value is lower than the standard value. The "specific disease" herein means, for example, lymphocytic adenohypophysitis, IgG4-related hypophysitis accompanied by diabetes insipidus, and tumor lesion accompanied by diabetes insipidus (the same applies to the following examples).

(Example of Qualitative Determination 2: Discrimination)

The determination that "the developed disease is LINH" is made when reactivity is found (positive), and the determination that "the developed disease is not LINH" is made when no reactivity is found (negative). When discrimination from a specific disease is made, in typical cases, the determination that "the developed disease is LINH" is made when reactivity is found (positive), and the determination that "the developed disease is the specific disease" is made when no reactivity is found (negative).

(Example of Qualitative Determination 3: Possibility of Developing LINH)

The determination that "the possibility of having LINH is high" is made when the detected value (for example, labeled amount or fluorescence amount) is higher than the standard value, and the determination that "LINH is not developed" or "the possibility of not having LINH is high" is made when the detected value is lower than the standard value. When determining the possibility of developing the disease in future, the determination that "LINH will be developed" or "the possibility of developing LINH is high" is made when the detected value is higher than the standard value, and the determination that "LINH will not be developed" or "the possibility of not developing LINH is high" is made when the detected value is lower than the standard value.

(Example of Qualitative Determination 4: Possibility of Developing LINH)

The determination that "LINH is developed" or "the possibility of having LINH is high" is made when reactivity is found (positive), and the determination that "LINH is not developed" or "the possibility of not having LINH is high" is made when no reactivity is found (negative). When determining the possibility of developing the disease in future, the determination that "LINH will be developed" or "the possibility of developing LINH is high" is made when reactivity is found (positive), and the determination that "LINH will not be developed" or "the possibility of not developing LINH is high" is made when no reactivity is found (negative).

(Example of Qualitative Determination 1: Discrimination)

As shown below, "the possibility that the developed disease is LINH (%)" is established for each range of the detected value, and "the possibility that the developed disease is LINH (%)" is determined from the detected value.

Detected values a to b: the possibility of LINH is 10% or less

Detected values b to c: the possibility of LINH is from 10% to 30%

Detected values c to d: the possibility of LINH is from 30% to 50%

Detected values d to e: the possibility of LINH is from 50% to 70%

Detected values e to f: the possibility of LINH is from 70% to 90%

(Example of Qualitative Determination 2: Possibility of Developing LINH)

As shown below, "the possibility of developing LINH (%)" is established for each range of the measured value, and "the possibility of developing LINH (%)" is determined from the measured value.

Measured values a to b: the possibility of developing LINH is 10% or less

Measured values b to c: the possibility of developing LINH is from 10% to 30%

Measured values c to d: the possibility of developing LINH is from 30% to 50%

Measured values d to e: the possibility of developing LINH is from 50% to 70%

Measured values e to f: the possibility of developing LINH is from 70% to 90%

The number of determination categories, and the biomarker level and determination result associated with each determination category will not be limited to the above examples, and may be freely established based on, for example, preliminary experiments. For example, the "threshold" when making the determination (discrimination) whether LINH or not using a predetermined threshold as the boundary or determining the level of the possibility of developing LINH, and the "biomarker level range" associated with the category according to the determination (discrimination) whether LINH or not, or the level of the possibility of developing LINH may be established based on statistical analysis using many specimens.

According to one embodiment of the present invention, the biomarker level measured at one point is compared with the biomarker level measured in the past in the same subject, thereby determining the presence or absence of the fluctuations and/or the degree of fluctuations in the biomarker level. The data thus obtained regarding the change in the biomarker level is useful information for monitoring the presence or absence of the development of LINH or the possibility of developing LINH, grasping the therapeutic effect, or estimating prognosis. Specifically, for example, on the basis of the fluctuation in the biomarker level, the increase, decrease, or no change in the possibility of developing LINH from the last test to the present test can be determined. If this evaluation is carried out in parallel with the treatment of LINH, the therapeutic effect can be confirmed, and the sign of recurrence of LINH can be grasped in advance. This allows the determination of more suitable course of treatment. In this manner, the present invention will markedly contribute to the maximization of the therapeutic effect and the improvement of patient's QOL (quality of life).

(Third Aspect of the Present Invention: Reagent and Kit for Testing the Possibility of Developing LINH)

The present invention further provides a reagent and kit used for the assay of LINH. The reagent of the present invention includes rabphilin 3a or its antibody-binding fragment (hereinafter referred to as "active ingredient"), which is a substance showing specific binding properties to the biomarker of the present invention. The active ingredient of the reagent of the present invention can be prepared in the form of, for example, a recombinant protein. For example, it can be prepared by transforming an appropriate host cell with a DNA which codes the target active ingredient (rabphilin 3a or its antibody-binding fragment), and collecting the protein expressed in the transformant. The collected protein is purified as appropriate according to the intended use. In this manner, various modifications can be made by obtaining a binding molecule as a recombinant protein. For example, the active ingredient composed of a recombinant protein linked to any desired peptide can e obtained by inserting a DNA coding a binding molecule and other appropriate DNA into the same vector, and producing a recombinant protein using the vector. Alternatively, modification which causes the addition of a sugar chain and/or lipid, or processing of N-terminal or C-terminal may be made. These modifications allow extraction of a recombinant protein, simplification of purification, or addition of biological function. The method for preparing the active ingredient is not limited to genetic engineering method. For example, the active ingredient of the reagent of the present invention may be prepared from a natural material using a standard method (for example, fracturing, extraction, or purification).

The active ingredient may be prepared using a cell-free synthesis system. The cell-free synthesis system (cell-free transcription system, cell-free transcription/translation system) synthesizes an mRNA or protein in vitro from the nucleic acid (DNA or mRNA) template coding for it, using not living cells but the ribosome or transcription/translation factor derived from living cells (or obtained by an genetic engineering method). The cell-free synthesis system commonly uses a cell extract obtained by purifying a cell lysate as necessary. The cell extract commonly contains ribosome, various factors such as an initiation factor, and various enzymes such as tRNA necessary for protein synthesis. When protein synthesis is carried out, other substances necessary for protein synthesis, such as energy sources including various amino acids, ATP, and GTP, and creatine phosphate are added to the cell extract. As a matter of course, during the protein synthesis, ribosome prepared separately, various factors, and/or various enzymes may be added as necessary.

Development of a transcription/translation system constructed by reconstituting various molecules (factors) necessary for protein synthesis was reported (Shimizu, Y. et al.: Nature Biotech., 19, 751-755, 2001). In this synthesis system, the genes of 31 factors composing the protein synthesis system of a bacterium, which includes three initiation factors, three elongation factors, four factors involved with termination, 20 aminoacyl-tRNA synthases which make an amino acid bind to tRNA, and methionyl tRNA formyl transferase are amplified from Escherichia coli, and a protein synthesis system is reconstituted using them in vitro. The present invention may use such a reconstituted synthesis system.

The cell-free protein synthesis system has the following advantages. Firstly, the system does not require the maintenance of living cells, so that provides good operability and a high degree of freedom. Accordingly, synthesis systems variously corrected and modified according to the properties of the intended protein can be designed. Secondly, a cell-based synthesis system basically cannot synthesize a protein toxic to the cells contained in the system, but a cell-free system can produce such a toxic protein. Furthermore, many proteins can be synthesized simultaneously and quickly, which facilitates high throughput. This system has an advantage that it allows easy separation and purification of produced proteins, which is advantageous for high throughput. The system also has an advantage that it can synthesize nonnatural proteins by the uptake of nonnatural amino acids.

Examples of the cell-free protein synthesis system widely used at present include the followings. More specifically, an Escherichia coli S30 extract system (procaryotic cell system), a wheat germ extract system (eucaryotic cell system), and a solubilized rabbit reticulocyte system (eucaryotic cell system). These systems are commercially available in the form of kits, and can be easily used.

The wheat germ extract system has an advantage that it can efficiently synthesizes high quality eucaryotic proteins, and is often used for synthesizing eukaryotic proteins which are difficult to be synthesized by the Escherichia coli S30 extract system. Recently, it was reported that a highly efficient and stable synthesis system is constructed by preparing an extract from the germ from which the seed albumen component has been removed by washing, and receives widespread attention (Madin, K. et al.: Proc. Natl. Acad. Sci. USA, 97: 559-564, 2000). Thereafter, techniques such as an untranslated mRNA sequence having high translation promotion capacity, a protein synthesis method using PCR for multi-item function analysis, and construction of special high expression vectors are developed (Sawasaki, T. et al.: Proc. Natl. Acad. Sci. USA, 99: 14652-14657, 2002), and are expected to be applied to various fields.

The wheat germ extract can be obtained by centrifuging ground wheat germ, and then separating the supernatant liquid by gel filtration. The translation reaction may refer to the method of Anderson et al. (Anderson, C. W. et al.: Methods Enzymol., 101, 638-644 (1983)). Improved methods are also reported, and for example, the method of Kawarasaki et al. (Kawarasaki, Y. et al.: Biotechnol. Prog., 16, 517-521 (2000)) and the method of Madin et al. (Madin, K. et al.: Proc. Natl. Acad. Sci. USA, 97: 559-564, 2000) may be referred to. For the wheat germ extract system, refer to WO 00/68412 A1, WO 01/27260 A1, WO 2002/024939 A1, WO 2005/063979 A1, Japanese Unexamined Patent Application Publication No. 6-7134, Japanese Unexamined Patent Application Publication No. 2002-529531, Japanese Unexamined Patent Application Publication No. 2005-355513, Japanese Unexamined Patent Application Publication No. 2006-042601, Japanese Unexamined Patent Application Publication No. 2007-097438, and Japanese Unexamined Patent Application Publication No. 2008-029203.

The cell-free synthesis system used for carrying out the present invention is not limited to the above-described one, and may be a system constructed based on, for example, an extract of a bacterium other than Escherichia coli, a plant other than wheat, an extract derived from an insect, an extract from animal cells, or genome information.

By labeling the active ingredient of the reagent of the present invention, the amount of the bound antibody can be directly detected using the labeled amount as the indicator. This allows the construction of a more simple assay. On the other hand, the use of an indirect detection method, such as a method using a secondary antibody bound to a labeling agent, or a method using a polymer bound to a secondary antibody and a labeling agent is also preferred from the viewpoint of detection sensitivity.

Examples of the labeling agent include enzymes such as peroxidase, microperoxidase, horseradish peroxidase (HRP), alkaline phosphatase, β-D-galactosidase, glucose oxidase, and glucose-6-phosphate dehydrogenase, fluorescent substances such as fluorescein isothiocyanate (FITC), tetramethylrhodamineisothiocyanate (TRITC), and europium, chemiluminescence substances such as luminol, isoluminol, and acridinium derivatives, coenzymes such as NAD, biotin, and radioactive materials such as $^{131}$I and $^{125}$I.

According to one embodiment, the reagent of the present invention is solid-phased according to the use application. The insoluble support used for making the solid phase is not particularly limited. For example, the insoluble support may be composed of a water-insoluble substance, such as a resin including a polystyrene resin, a polycarbonate resin, a silicon resin, a nylon resin, and glass. Loading on the insoluble support may be achieved by physical adsorption or chemical adsorption.

The kit of the present invention includes the reagent of the present invention as a main component. The kit may further include other reagent used for carrying out the assay (for example, a buffer solution, a blocking reagent, an enzyme substrate, and a color-producing reagent) and/or an apparatus or instrument (for example, a container, a reaction apparatus, and a fluorescence reader). In addition, the kit preferably includes the active ingredient of the reagent of the present invention (rabphilin 3a or its antibody-binding fragment) as the standard sample. In addition, usually, an instruction manual is attached to the kit of the present invention.

Example

1. Search of LINH-Specific Antigen

The blood serums of LINH patients, the blood serums of disease control subjects with diabetes insipidus accompanying cerebral tumor and others, and the blood serums of healthy subjects were collected, and IgG was purified by ordinary procedure. On the other hand, an extract of posterior pituitary protein was purified from rat pituitary. The purified IgG was mixed with the extract of posterior pituitary protein, the mixture was subjected to immunoprecipitation using protein G beads, and then an antigen was eluted from the immune precipitate. The eluted antigen was reduced, alkylated, and then subjected to trypsin digestion (in-solution digestion). The sample thus prepared was subjected to analysis (shotgun proteomics) using an LC-MS/MS system, Pradigm MS4-PAL-LTQ Orbitrap XL (Thermo Fisher Scientific Inc.). The MS data thus obtained was analyzed based on NCBI RefSeq and Swiss Prot database, using Mascot (Matrix Science Ltd.) software. As a result of the analysis, six autoantigen protein candidates were identified.

2. Reactivity Between LINH-Specific Antigen and Blood Serums of Patients (1) Western Blot Subsequently, six proteins as autoantigen protein candidates were subcloned into an expression vector (pcDNA3.1D/V5-His-TOPO (registered trademark)). Thereafter, the expression vector was transfected into a mammal cell line (HEK293FT) using Lipofectamine 2000 (registered trademark), thereby synthesizing recombinant proteins. Six recombinant proteins of autoantigen candidates synthesized using the HEK293FT cells were separated by SDS-polyacrylamide electrophoresis (PAGE), and the reactivity between the blood serums of the patients and recombinant proteins was studied by the Western blot using the blood serums of the patients as the primary antibodies. The blood serums used in the study are as follows:

| | |
|---|---|
| (a) LINH | 9 subjects |
| (b) Lymphocytic adenohypophysitis (LAH) | 3 subjects |
| (c) IgG4-related hypophysitis | 3 subjects |
| (d) Disease control | (10 subjects in total) |
| Germ cell tumor + diabetes insipidus (DI) | 3 subjects |
| After surgery of suprasellar pineal tumor + DI | 1 subject |
| After surgery of hypothalamus tumor + DI | 1 subject |
| Rathke's cleft cyst + DI | 1 subject |
| Craniopharyngioma + DI | 2 subjects |
| After surgery of glioma + DI | 1 subject |
| Sarcoidosis + DI | 1 subject |
| (e) Healthy control (healthy subject) | 10 subjects |

The results of the Western blot (representative examples) are shown in FIG. 1. In eight of the nine patients with LINH (8/9), an autoantibody against rabphilin 3a, which is a 76 kDa protein, was found. On the other hand, the subject in whom an autoantibody was found in the control was 1/10 for the healthy subjects, 0/3 for the lymphocytic adenohypophysitis subjects, 1/3 for the subjects with IgG4-related hypophysitis accompanied by diabetes insipidus, and 1/10 for the subjects with diabetes insipidus accompanying tumor (FIG. 2). For all the studied subjects, sensitivity of the autoantibody was 88.9% (8/9), specificity was 87.0% (20/23) (88.5% (23/26) when the subjects with IgG4-related hypophysitis were added), and specificity of 90% (9/10) was shown in the discrimination from the subjects with DI accompanying tumor lesion, which is difficult to be clinically discriminated from LINH (FIG. 2).

(2) Immunohistochemistry

Figure 3:
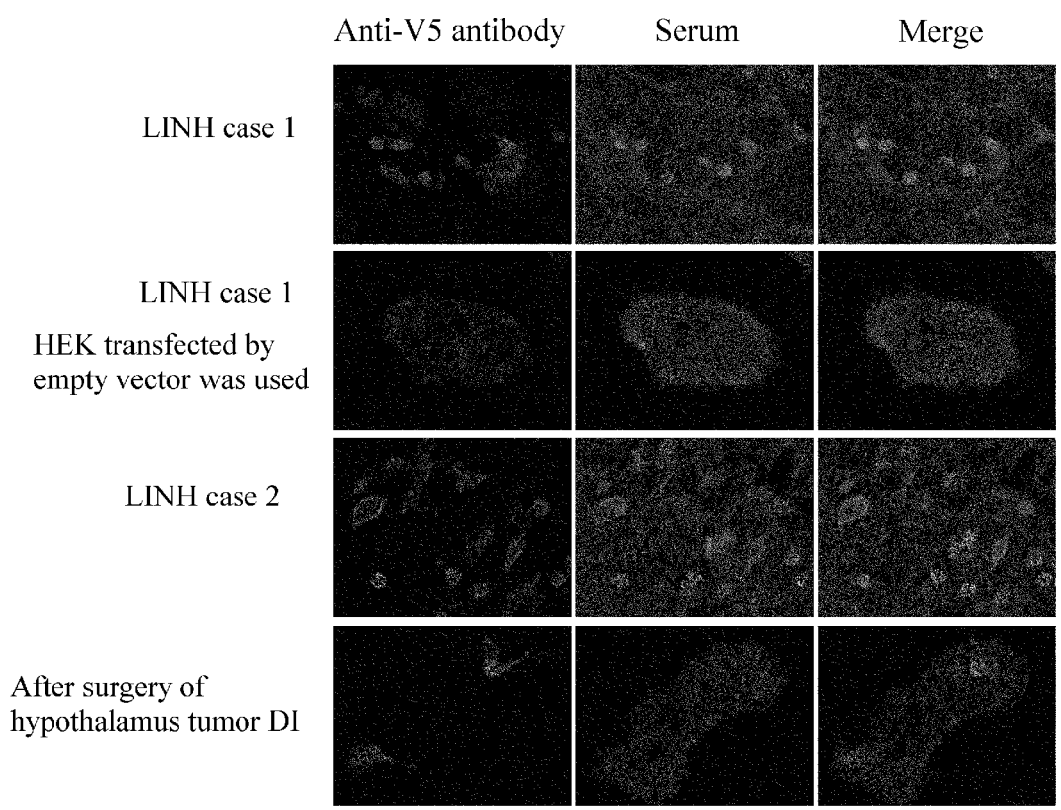
FIG. 3 shows the reactivity between the HEK293FT cells which had been transfected with rabphilin 3a and the blood serums of LINH patients (result of immunohistochemistry). The reactivity to an anti-V5 antibody (left), reactivity to the blood serums (center), and the merge of two images (right) are shown.

The reactivity between the HEK293FT cells transfected with rabphilin 3a and the blood serum of an LINH patient was studied by immunohistochemistry. The results are shown in FIG. 3. The LINH blood serum (the highest row) showed reactivity in agreement with the cells recognized by the anti-V5 antibody (colocalization). When the blood serum of other LINH patient was used (third row from the top), the same staining property was found. On the other hand, when an empty vector was transfected (the second row from the top), no reaction was found neither of the anti-V5 antibody nor blood serum. When the blood serum of a patient with diabetes insipidus after tumor surgery was used (the lowest row), no colocalization was found, and it was suggested that the antibody against rabphilin 3a is specific to the patients with LINH.

3. Expression of LINH-Specific Antigen

The expression of rabphilin 3a in the vasopressin (AVP) neurons in the rat posterior pituitary and hypothalamic supraoptic nucleus (SON) was studied by immunohistochemistry (double staining by an anti-AVP antibody and anti-rabphilin antibody). The result of immunohistochemistry is shown in FIG. 4. The expression of rabphilin 3a was found in the AVP neurons in the posterior pituitary and hypothalamus SON. The fact that the expression of rabphilin 3a was found in the lesion region of LINH strongly suggests that the possibility of involvement of the protein in the disease state of LINH.

4. Summary

The LINH-specific antigen protein rabphilin 3a was successfully found. The anti-rabphilin 3a antibody is used as a biomarker for LINH. The use of the anti-rabphilin 3a antibody as the indicator allows the test of LINH with markedly high sensitivity and specificity (for example, discrimination). The anti-rabphilin 3a antibody is also useful for grasping the disease state of LINH.

5. Study Using More Specimens (Including Specimens of Other Autoimmune Diseases)

The type of the specimen and subject was increased, and usefulness of the anti-rabphilin 3a antibody as a biomarker was further studied. The results are shown in FIGS. 5 and 6. The specificity was as high as 92.8% and 95.2% for the discrimination between the diabetes insipidus accompanying tumor lesion and LINH, and the discrimination between idiopathic or secondary central diabetes insipidus and LINH, respectively, and a high specificity (89.9%) was exhibited for the discrimination between various autoimmune diseases and LINH. Accordingly, more specifically, it was supported that the anti-rabphilin 3a antibody is markedly useful as a biomarker for LINH.

INDUSTRIAL APPLICABILITY

In the assay of the present invention, discrimination of LINH and others are carried out using the anti-rabphilin 3a antibody as the indicator. According to the assay of the present invention, LINH can be discriminated with markedly high sensitivity and specificity. Accordingly, the assay of the present invention can be regarded as markedly useful for the prevention of erroneous diagnosis, and determination of appropriate course of treatment.

This invention will not be limited to the embodiments and examples of the present invention. Various modifications

[Sequence List]

The invention claimed is:

1. An assay for the discrimination of lymphocytic infundibuloneurohypophysitis, the assay comprising the following steps (a) to (c):
   (a) a step of providing a specimen derived from a subject suspected of having lymphocytic infundibuloneurohypophysitis, wherein the specimen is blood, plasma, serum, or cerebrospinal fluid;
   (b) a step of detecting an anti-rabphilin 3a antibody in the specimen with a labeled rabphilin 3a or a labeled antibody binding fragment of rabphilin 3a; and
   (c) a step of determining whether the subject has lymphocytic infundibuloneurohypophysitis, or the subject has the possibility of developing lymphocytic infundibuloneurohypophysitis, wherein the subject has infundibuloneurohypophysitis or the subject has the possibility of developing lymphocytic infundibuloneurohypophysitis when the detection result of step (b) is greater than a standard value, a control value, or a value of a previous specimen taken from the subject.

2. The assay of claim 1, wherein detecting the anti-rabphilin 3a antibody comprises a measurement method selected from fluoroimmunoassay, enzyme immunoassay, and radioimmunoassay.

3. The assay of claim 1, wherein the label is an enzyme, a fluorescent substance, chemiluminescence substance, biotin, coenzyme or radioactive material.

4. The assay of claim 3, wherein the enzyme is selected from the group consisting of an peroxidase, microperoxidase, horseradish peroxidase, alkaline phosphatase, β-D-galactosidase, glucose oxidase, and glucose-6-phosphate dehydrogenase.

5. The assay of claim 3, wherein the fluorescent substance is fluorescein isothiocyanate, tetramethylrhodamineisothiocyanate, or europium.

6. The assay of claim 3, wherein the chemiluminescence substance is luminol, isoluminol, or acridinium derivatives.

7. The assay of claim 3, wherein the coenzyme is nicotinamide adenine dinucleotide (NAD).

8. The assay of claim 3, wherein the radioactive material is $^{131}$I or $^{125}$I.

9. The assay of claim 1, wherein the labeled rabphilin 3a is a antibody-binding fragment of a rabphilin 3a protein.

10. An assay for lymphocytic infundibuloneurohypophysitis, the method comprising the following steps (a) to (c):
    (a) a step of providing a specimen derived from a subject suspected of having lymphocytic infundibuloneurohypophysitis, wherein the specimen is blood, plasma, serum, or cerebrospinal fluid;
    (b) a step of detecting an anti-rabphilin 3a antibody in the specimen with a latex bead coated with rabphilin 3a or antibody binding fragment of rabphilin 3a; and
    (c) a step of determining whether the subject has lymphocytic infundibuloneurohypophysitis, or the subject has the possibility of developing lymphocytic infundibuloneurohypophysitis, wherein the subject has infundibuloneurohypophysitis or the subject has the possibility of developing lymphocytic infundibuloneurohypophysitis when the detection result of step (b) is greater than a standard value, a control value, or a value of a previous specimen taken from the subject.

11. The assay of claim 10, wherein detecting the anti-rabphilin 3a antibody comprises a latex agglutination assay.

* * * * *

```
                         SEQUENCE LISTING

<160> NUMBER OF SEQ ID NOS: 2

<210> SEQ ID NO 1
<211> LENGTH: 690
<212> TYPE: PRT
<213> ORGANISM: Homo sapiens

<400> SEQUENCE: 1

Met Thr Asp Thr Val Phe Ser Asn Ser Ser Asn Arg Trp Met Tyr Pro
1               5                   10                  15

Ser Asp Arg Pro Leu Gln Ser Lys Leu Gln Ala Gly Trp Ser Val His
            20                  25                  30

Pro Gly Gly Gln Pro Asp Arg Gln Arg Lys Gln Glu Glu Leu Thr Asp
        35                  40                  45

Glu Glu Lys Glu Ile Ile Asn Arg Val Ile Ala Arg Ala Glu Lys Met
50                  55                  60

Glu Glu Met Glu Gln Glu Arg Ile Gly Arg Leu Val Asp Arg Leu Glu
65                  70                  75                  80

Asn Met Arg Lys Asn Val Ala Gly Asp Gly Val Asn Arg Cys Ile Leu
                85                  90                  95

Cys Gly Glu Gln Leu Gly Met Leu Gly Ser Ala Cys Val Val Cys Glu
            100                 105                 110

Asp Cys Lys Lys Asn Val Cys Thr Lys Cys Gly Val Glu Thr Asn Asn
        115                 120                 125

Arg Leu His Ser Val Trp Leu Cys Lys Ile Cys Ile Glu Gln Arg Glu
    130                 135                 140

Val Trp Lys Arg Ser Gly Ala Trp Phe Phe Lys Gly Phe Pro Lys Gln
145                 150                 155                 160

Val Leu Pro Gln Pro Met Pro Ile Lys Lys Thr Lys Pro Gln Gln Pro
                165                 170                 175

Val Ser Glu Pro Ala Ala Pro Glu Gln Pro Ala Pro Glu Pro Lys His
            180                 185                 190

Pro Ala Arg Ala Pro Ala Arg Gly Asp Ser Glu Asp Arg Arg Gly Pro
        195                 200                 205

Gly Gln Lys Thr Gly Pro Asp Pro Ala Ser Ala Pro Gly Arg Gly Asn
    210                 215                 220

Tyr Gly Pro Pro Val Arg Arg Ala Ser Glu Ala Arg Met Ser Ser Ser
225                 230                 235                 240

Ser Arg Asp Ser Glu Ser Trp Asp His Ser Gly Gly Ala Gly Asp Ser
                245                 250                 255

Ser Arg Ser Pro Ala Gly Leu Arg Arg Ala Asn Ser Val Gln Ala Ser
            260                 265                 270

Arg Pro Ala Pro Gly Ser Val Gln Ser Pro Ala Pro Pro Gln Pro Gly
        275                 280                 285

Gln Pro Gly Thr Pro Gly Gly Ser Arg Pro Gly Pro Gly Pro Ala Gly
    290                 295                 300

Arg Phe Pro Asp Gln Lys Pro Glu Val Ala Pro Ser Asp Pro Gly Thr
305                 310                 315                 320

Thr Ala Pro Pro Arg Glu Glu Arg Thr Gly Val Gly Gly Tyr Pro
                325                 330                 335

Ala Val Gly Ala Arg Glu Asp Arg Met Ser His Pro Ser Gly Pro Tyr
```

```
                    340                 345                 350
    Ser Gln Ala Ser Ala Ala Ala Pro Gln Pro Ala Ala Arg Gln Pro
            355                 360                 365

Pro Pro Pro Glu Glu Glu Glu Glu Ala Asn Ser Tyr Asp Ser Asp
        370                 375                 380

Glu Ala Thr Thr Leu Gly Ala Leu Glu Phe Ser Leu Leu Tyr Asp Gln
    385                 390                 395                 400

Asp Asn Ser Ser Leu Gln Cys Thr Ile Ile Lys Ala Lys Gly Leu Lys
                    405                 410                 415

Pro Met Asp Ser Asn Gly Leu Ala Asp Pro Tyr Val Lys Leu His Leu
                420                 425                 430

Leu Pro Gly Ala Ser Lys Ser Asn Lys Leu Arg Thr Lys Thr Leu Arg
                435                 440                 445

Asn Thr Arg Asn Pro Ile Trp Asn Glu Thr Leu Val Tyr His Gly Ile
            450                 455                 460

Thr Asp Glu Asp Met Gln Arg Lys Thr Leu Arg Ile Ser Val Cys Asp
    465                 470                 475                 480

Glu Asp Lys Phe Gly His Asn Glu Phe Ile Gly Glu Thr Arg Phe Ser
                    485                 490                 495

Leu Lys Lys Leu Lys Pro Asn Gln Arg Lys Asn Phe Asn Ile Cys Leu
                500                 505                 510

Glu Arg Val Ile Pro Met Lys Arg Ala Gly Thr Thr Gly Ser Ala Arg
                515                 520                 525

Gly Met Ala Leu Tyr Glu Glu Glu Val Glu Arg Val Gly Asp Ile
            530                 535                 540

Glu Glu Arg Gly Lys Ile Leu Val Ser Leu Met Tyr Ser Thr Gln Gln
    545                 550                 555                 560

Gly Gly Leu Ile Val Gly Ile Ile Arg Cys Val His Leu Ala Ala Met
                    565                 570                 575

Asp Ala Asn Gly Tyr Ser Asp Pro Phe Val Lys Leu Trp Leu Lys Pro
                580                 585                 590

Asp Met Gly Lys Lys Ala Lys His Lys Thr Gln Ile Lys Lys Lys Thr
                595                 600                 605

Leu Asn Pro Glu Phe Asn Glu Glu Phe Phe Tyr Asp Ile Lys His Ser
            610                 615                 620

Asp Leu Ala Lys Lys Ser Leu Asp Ile Ser Val Trp Asp Tyr Asp Ile
    625                 630                 635                 640

Gly Lys Ser Asn Asp Tyr Ile Gly Gly Cys Gln Leu Gly Ile Ser Ala
                    645                 650                 655

Lys Gly Glu Arg Leu Lys His Trp Tyr Glu Cys Leu Lys Asn Lys Asp
                660                 665                 670

Lys Lys Ile Glu Arg Trp His Gln Leu Gln Asn Glu Asn His Val Ser
                675                 680                 685

Ser Asp
        690

<210> SEQ ID NO 2
<211> LENGTH: 865
<212> TYPE: DNA
<213> ORGANISM: Homo sapiens

<400> SEQUENCE: 2
atgactgaca  ccgtgttcag  caacagttct  aaccgttgga  tgtacccag  tgaccggccc      60 cttcaatcaa  agctccaggc  aggctggtcc  gtccacccg  gtggtcagcc  tgacaggcag     120
```

```
aggaagcagg aagagctgac tgatgaggag aaagaaatca tcaacagggt gattgctcga    180
gctgagaaaa tggaagagat ggagcaggag cgaatcggac gcctggtgga ccgcctagaa    240
aacatgagga agaacgtggc tggagatggg gtgaaccgct gcatactgtg tggagaacag    300
ctggggatgc tgggctctgc ctgtgtagta tgtgaggact gtaagaagaa cgtctgcacc    360
aagtgcggag tggagaccaa caaccgcctg cattctgtgt ggctctgcaa aatctgcatt    420
gagcagaggg aggtgtggaa gcgttctgga gcgtggttct tcaaaggctt ccccaaacag    480
gtcctcccac agcctatgcc tataaagaag accaagcccc agcagcctgt cagtgagcct    540
gctgcccctg aacagcctgc tcctgagccc aagcaccctg cccgggctcc agctcgaggt    600
gacagtgaag ataggagggg cccgggtcag aagacaggcc ctgacccagc ctctgctccc    660
gggcgaggaa actatgggcc tcccgtgcgc agggcctccg aggcacgaat gagctcatct    720
agccgagatt cagagagctg ggaccacagt gggggtgctg gagactccag ccggagccca    780
gcaggtttga gacgggccaa ctcagtccag gcctccagac ctgccccagg ctcggtgcag    840
agcccagcgc cacctcagcc tgggc                                          865
```